United States Patent [19]

Drivas

[11] Patent Number: 5,685,842
[45] Date of Patent: Nov. 11, 1997

[54] DRUG DELIVERY SYSTEM AND METHOD

[75] Inventor: Nicoloas A. Drivas, Des Plaines, Ill.

[73] Assignee: Abbott Laboratories, Abbott Park, Ill.

[21] Appl. No.: 635,983

[22] Filed: Apr. 22, 1996

[51] Int. Cl.⁶ .................................................. A61M 31/00
[52] U.S. Cl. ........................... 604/49; 604/201; 604/283; 604/905
[58] Field of Search ................................. 604/49, 86, 88, 604/240, 241, 243, 201, 206, 283, 905

[56] References Cited

U.S. PATENT DOCUMENTS

| | | | |
|---|---|---|---|
| 5,215,538 | 6/1993 | Larkin | 604/283 X |
| 5,356,396 | 10/1994 | Wyatt et al. | 604/905 X |
| 5,376,073 | 12/1994 | Graves et al. | 604/86 |
| 5,501,676 | 3/1996 | Neidospial et al. | 604/283 |
| 5,514,117 | 5/1996 | Lynn | 604/283 |

Primary Examiner—John D. Yasko
Attorney, Agent, or Firm—Brian R. Woodworth

[57] ABSTRACT

A fluid delivery set for delivering fluid from a primary container to a patient. The set includes a conduit defining a fluid flow path. A first connector constructed to be fluidly connected to a primary container is mounted on a first end portion of the conduit. A second connector is mounted on a second end portion of the conduit. The second connector includes a first end portion and a second end portion, the first end portion of the second connector being mounted on the second end portion of the conduit. The second connector defines a fluid flow path therethrough. A pierceable seal is disposed in and fluidly seals the fluid flow path defined through the second connector. The second connector further includes a piercing member having a piercing tip. The piercing tip is constructed to pierce the pierceable member when relative movement is effected between the pierceable member and the piercing member, whereupon fluid communication is established through the pierceable seal.

11 Claims, 3 Drawing Sheets

DRUG DELIVERY SYSTEM AND METHOD

TECHNICAL FIELD

This invention relates to an improved system for delivering a pharmaceutical product to a patient. In particular, the present invention is directed to a system and method for delivering an imaging agent from a primary container to a transfer set which in turn delivers the imaging agent to the patient.

BACKGROUND OF THE INVENTION

Tube sets are commonly used for the purpose of delivering liquid pharmaceutical products from a primary container to a patient. These tube sets have a wide variety of configurations adapted to the intended function of the tube set. Tube sets typically include a connector constructed to provide fluid communication between a primary fluid container and the tube set. For example, piercing pins or spikes are commonly used to pierce a seal provided on the primary fluid container in order to provide a direct, fluid connection between the container and the tube set. The connector is typically connected fluidly to a tube configured to deliver the fluid to the patient. A variety of flow restrictors, connectors, and valves are included along the length of the tube dependent upon the intended function of the tube set.

U.S. Pat. No. 5,334,170 to Moroski discloses a tube set configured to permit the primary fluid container to be used in more than a single procedure, thereby reducing waste of the liquid pharmaceutical product contained in the primary fluid container. Tube sets of the type disclosed in U.S. Pat. No. 5,334,170 include two portions, i.e., an access set and a transfer set, that are configured to be releasably connected to one another. The connection between the respective portions of the tube set is typically effected using a luer or a locking luer type connection. Such a connection is effected by providing a male luer member on one portion of the tube set and a mating female luer member on the other portion of the tube set. A locking luer connection can be effected by providing mating threads on the male and female luer members and/or on the respective tube portions.

Although tube sets of the type disclosed in U.S. Pat. No. 5,334,170 provide significant advantages over tube sets that do not permit re-use of the primary fluid container, it has been found that the luer connection between the respective tube portions can become stuck when a relatively sticky pharmaceutical product, e.g., an imaging agent, is flowed through the tube set. In particular, it has been found that in certain cases the imaging agent will tend to coat the outer wall of the male luer member and the inner wall of the female luer member, thereby causing the male and female luer members to become adhesively bonded to one another. Disconnection of the male and female members can be difficult, and in some cases impossible, when this occurs.

SUMMARY OF THE INVENTION

According to the present invention, an improved system is provided for delivering pharmaceutical products from a primary container to a patient. The system of the present invention includes a tubing member configured to transport a pharmaceutical fluid therethrough. The system further includes a first connector for establishing a fluid connection between the primary container and the tubing member, the first connector being mounted on a first end portion of the tubing member. The system further includes a second connecting member mounted on a second end portion of the tubing member. The second connecting member is configured to establish a fluid connection between the tubing member and a second tubing member. In a preferred embodiment, the second connecting member further is configured such that it connects to the second tubing member in substantial end-to-end abutment therewith.

The present invention also includes a method for delivering an imaging agent from a primary fluid container to a patient. The method includes the step of providing a system constructed in accordance with the present invention. The method further includes the step of fluidly connecting the system to a primary container containing an imaging agent by connecting the first connector to the primary fluid container. The method also includes the step of providing a second member configured to connect to the second tubing member, such connection preferably being substantially an end-to-end abutment therebetween. The second member is fluidly connected to the connecting member, preferably in substantial end-to-end abutment, thereby establishing a fluid flow path from the primary container to the second member.

BRIEF DESCRIPTION OF THE DRAWINGS

In the accompanying drawings that form part of the specification.

DESCRIPTION OF THE PREFERRED EMBODIMENT

While this invention is susceptible of embodiment in many different forms, this specification and the accompanying drawing disclose only one specific form as an example of the invention. The invention is not intended to be limited to the embodiment so described. The scope of the invention is pointed out in the appended claims.

For ease of description, the apparatus of this invention is described in the normal (upright) operating position, and terms such as upper, lower, horizontal, etc., are used with reference to this position. It will be understood, however, that the apparatus of this invention may be manufactured, stored, transported, and sold in an orientation other than the position described.

The figures illustrating the apparatus show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

The apparatus of this invention is used with certain conventional components the details of which, although not fully illustrated or described, will be apparent to those having skill in the art and an understanding of the necessary functions of such components.

Figure 1:
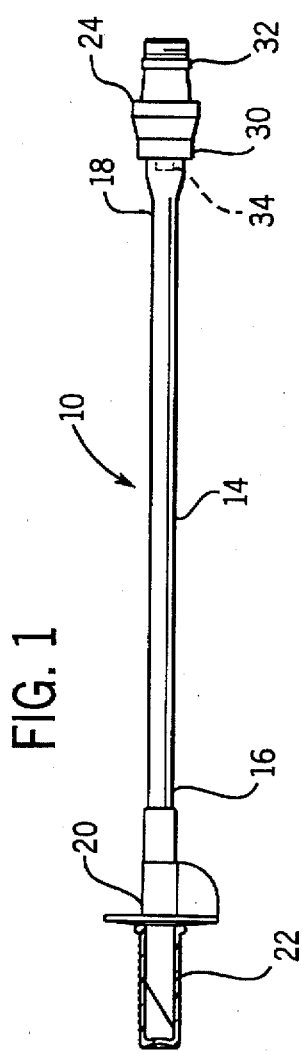
FIG. 1 is an elevational view of a tube set constructed in accordance with the present invention.
Figure 2:
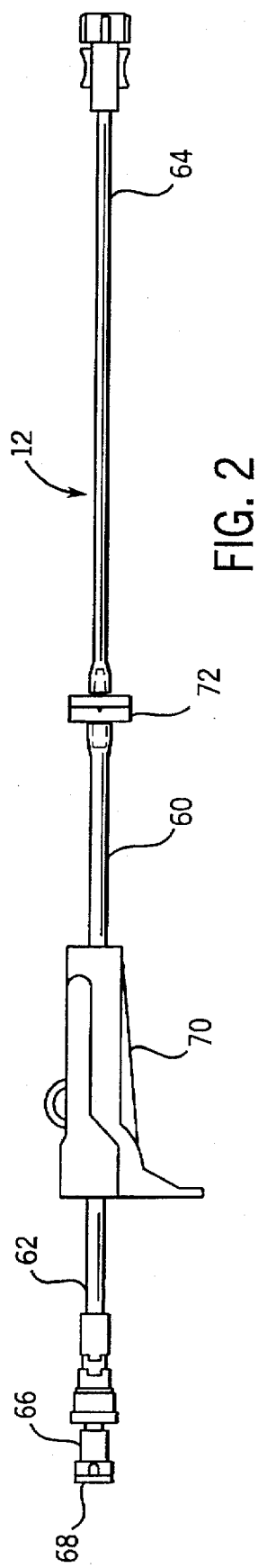
FIG. 2 is an elevational view of a transfer set constructed in accordance with the present invention.

A tube set constructed in accordance with the present invention includes access tube set 10, as depicted in FIG. 1, and transfer tube set 12, as depicted in FIG. 2. Access tube set 10 includes a conduit 14 having a first end portion 16 and a second end portion 18. Conduit 14 defines a fluid flow pathway therethrough. In the preferred embodiment of the present invention, conduit 14 and the fluid flow pathway defined thereby are substantially circular in cross-section such that conduit 14 is substantially annular in cross-section. However, the external dimension and configuration of conduit 14 and the inner dimension and configuration of the fluid flow pathway defined thereby can be varied to suit a variety of applications of access tube set 10. For example, where access tube set 10 is used to deliver an imaging agent such as iopamidol, conduit 14 can have an outer diameter of 0.17 inches and an inner diameter of 0.12 inches. It will be appreciated that conduit 14 and the fluid flow pathway defined thereby can have a variety of geometrical configurations, can be constructed of any material suitable for medical applications, and can have any dimension without departing from the scope of the present invention. The length of conduit 14 can be varied dependent upon the application in which access tube set 10 is to be used. In the preferred embodiment of the present invention, conduit 14 has a length in the range of substantially six inches to substantially eight inches.

First connector 20 is mounted on first end portion 16 of conduit 14. First connector 20 is constructed to provide a fluid connection between a primary fluid container (not pictured) and conduit 14. One of ordinary skill in the pertinent art will appreciate that the configuration of first connector 20 will be dependent upon the configuration of the primary fluid container. In the embodiment of the present invention depicted in FIG. 1, first connector 20 includes a piercing pin or spike 22 of known construction. In this embodiment, first connector 20 is constructed to pierce a primary fluid container, or a pierceable membrane mounted on the primary fluid container, in order to establish a fluid connection between the primary fluid container and the fluid flow pathway defined by conduit 14. Piercing pin 22 can be vented, for use with rigid primary fluid containers, or non-vented, for use with flexible primary fluid containers. In the preferred embodiment of the present invention, piercing pin 22 is configured for use as both a vented and a non-vented spike, thus eliminating the need for two different commercial embodiments of the present invention. Piercing pin 22 can be constructed of any material suitable for medical applications having sufficient rigidity to pierce the primary fluid container or a pierceable membrane associated therewith. Metals and hard plastics are particularly suitable for this purpose.

First connector 20 can have a variety of configurations other than spike 22. For example, first connector 20 can be configured to provide a luer or locking luer fitting where the primary fluid container has a mating luer member. In the alternative, first connector 20 can be a luer activated valve as disclosed in U.S. Pat. No. 5,215,538 where the primary fluid container has a luer member associated therewith. First connector 20 also can be a valved infusion port as disclosed in U.S. Pat. No. 5,049,128. A variety of other known connectors can be used in lieu of first connector 20 of the preferred embodiment depicted in FIG. 1 without departing from the intended spirit and scope of the present invention.

First connector 20 can be mounted on first end portion 16 of conduit 14 using known techniques. For example, first connector 20 can be adhesively or frictionally fitted on first end portion 16.

Figure 3:
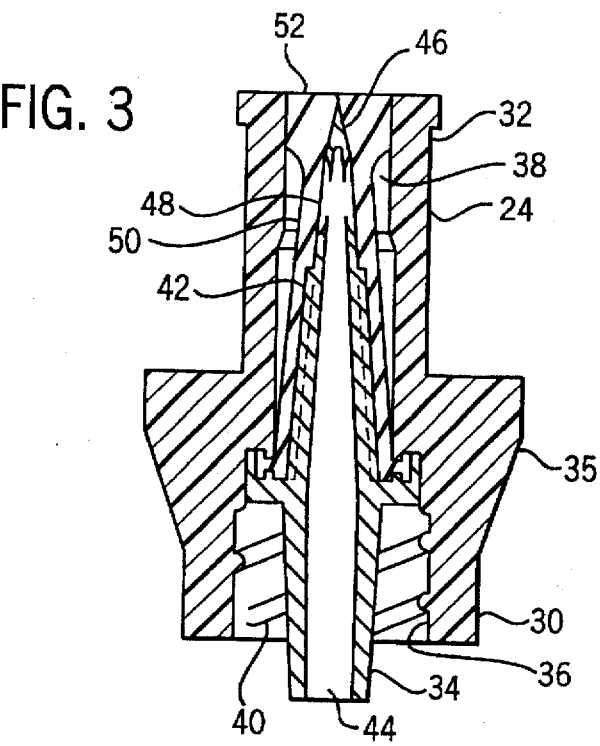
FIG. 3 is a cross-sectional view of a second connector with a pierceable closure in a first position in accordance with the present invention.

Second connector 24 is mounted on second end portion 18 of conduit 14. Second connector 24 as depicted in FIG. 3 has a first end portion 30 and a second end portion 32. First end portion 30 is configured to be connected to second end portion 18 of conduit 14. Second connector 24 also can be mounted on second end portion 18 of conduit 14 using known techniques. Second connector 24 establishes fluid communication between conduit 14 and a luer member or syringe inserted into second connector 24, as discussed in detail herein.

In the preferred embodiment of the present invention depicted in FIGS. 1 and 3, second connector 24 is a CLAVE™ needleless connector from ICU Medical, Inc. of San Clemente, Calif. Second connector 24 includes casing 35 which defines first and second chambers 36, 38 therein. In the preferred embodiment of the present invention depicted in the accompanying figures, first end portion 30 includes protruding member 34 which is positioned in and protrudes from first chamber 36. Protruding member 34 can be integrally formed on casing 35, or can be mounted thereon using known techniques that form no part of the present invention.

In the preferred embodiment of the present invention, protruding member 34 and second end portion 18 of conduit 14 are configured such that second end portion 18 of conduit 14 can be frictionally mounted on protruding member 34 by sliding second end portion 18 over the external surface of protruding member 34. Other methods, including the use of adhesives, can be employed to secure second end portion 18 of conduit 14 to first end portion 30 of second connector 24.

In a first alternative embodiment, first chamber 36 has threads 40 formed on an interior wall thereof. Threads 40 are configured to mate with threads formed on an exterior surface of second end portion 18 of conduit 14, or on a connector attached to second end portion 18 of conduit 14, such that conduit 14 can be threadingly secured to first end portion 30 of second connector 24. In a second alternative embodiment, threads are formed on an exterior surface of protruding member 34 and are configured to mate with threads formed on an interior surface of second end portion 18 of conduit 14, or on a connector attached to second end portion 18 of conduit 14, thereby allowing conduit 14 to be threadingly secured to first end portion 30 of second connector 24. One of ordinary skill in the art will appreciate that further methods for connecting second connector 24 to second end portion 18 of conduit 14 are possible without departing from the scope of the present invention.

Second connector 24 further includes a piercing member 42 disposed within second chamber 38. In the preferred embodiment of the present invention, piercing member 42 is mounted on protruding member 34 and casing 35. Piercing member 42 can be integrally formed with protruding member 34 and/or casing 35, or can be mounted thereon using known techniques. Piercing member 42 and protruding member 34 define fluid flow channel 44 therethrough, as depicted in FIG. 3.

Piercing member 42 includes a piercing tip 46 positioned within second chamber 38. Piercing member 42 defines aperture 48 therethrough whereby fluid flow channel 44 is in fluid communication with an external environment of piercing member 42 through aperture 48.

Figure 4:
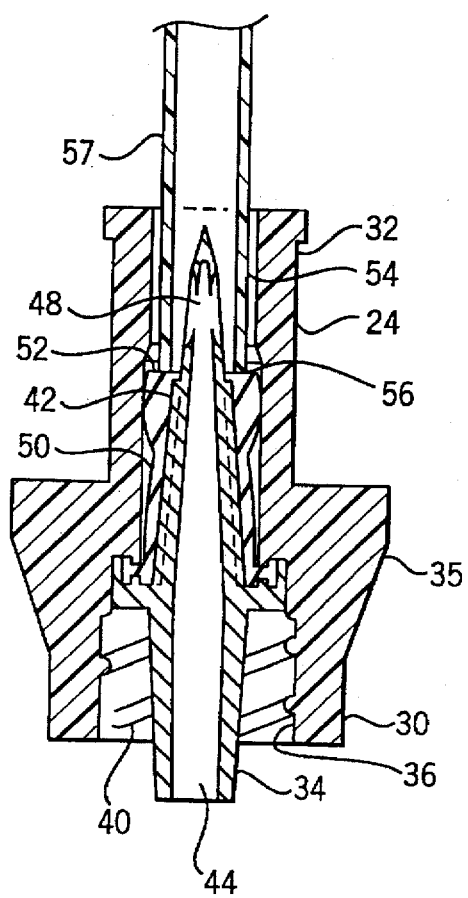
FIG. 4 is an cross-sectional view of a second connector with a pierceable closure in a second position in accordance with the present invention.

Pierceable closure 50 is positioned within second chamber 38 as depicted in FIG. 3. Pierceable closure 50 is constructed of a resilient material that is flexible, inert, impermeable to fluid, and pierceable by piercing tip 46. Pierceable closure 50 is movable between a first position depicted in FIG. 3 and a second position depicted in FIG. 4. Pierceable closure 50 is mounted on piercing member 42 and casing 35 such that first chamber 36 and second chamber 38 are fluidly isolated when pierceable closure 50 is in the first position depicted in FIG. 3. As depicted in FIG. 4, first chamber 36 and at least a portion of second chamber 38 are in fluid communication through fluid flow channel 44 when pierceable closure 50 is in the second position. Pierceable closure 50 can be mounted on casing 35 using a variety of known techniques that form no part of the present invention. In the preferred embodiment depicted in FIG. 3, pierceable closure 50 has a substantially flat upper surface 52 which is substantially co-planar with an edge of casing 35. However, it will be appreciated that pierceable closure 50 can have a variety of other configurations without affecting its utility and function in accordance with the present invention.

Second end portion 32 of second connector 24 preferably is configured to receive a male luer member or a syringe 54 therein. In an alternative embodiment, threads are formed on casing 35 at second end portion 32 such that a male luer member or a syringe 54 having mating threads can be threadingly secured thereto. When a male luer member or a syringe 54 is inserted into second end portion 32 of second connector 24, the male luer member or syringe 54 engages upper surface 52 of pierceable closure 50 and urges it towards first end portion 30. As pierceable closure 50 is moved towards first end portion 30, upper surface 52 of pierceable closure 50 is pierced by piercing tip 48. It will be appreciated that distal edge 56 of male luer member or syringe 54 will engage pierceable member 50 as male luer member or syringe 54 is urged into second end portion 32 of second connector 24. Due to the construction of pierceable member 50, distal edge 56 will be in substantial end-to-end abutment with pierceable member 50. As a result, exterior surface 57 of male luer member or syringe 54 will not exposed to the pharmaceutical fluid being transferred thereto under normal operating conditions. Thus, luer member or syringe 54 can be detached readily from second connector 24, even when a relatively viscous or sticky pharmaceutical product such as iopamidol is being transferred from second connector 24 to male luer member or syringe 54. In addition, pierceable member 50 will return substantially to its first position upon withdrawal of male luer member or syringe 54 from second connector 24.

Figure 5:
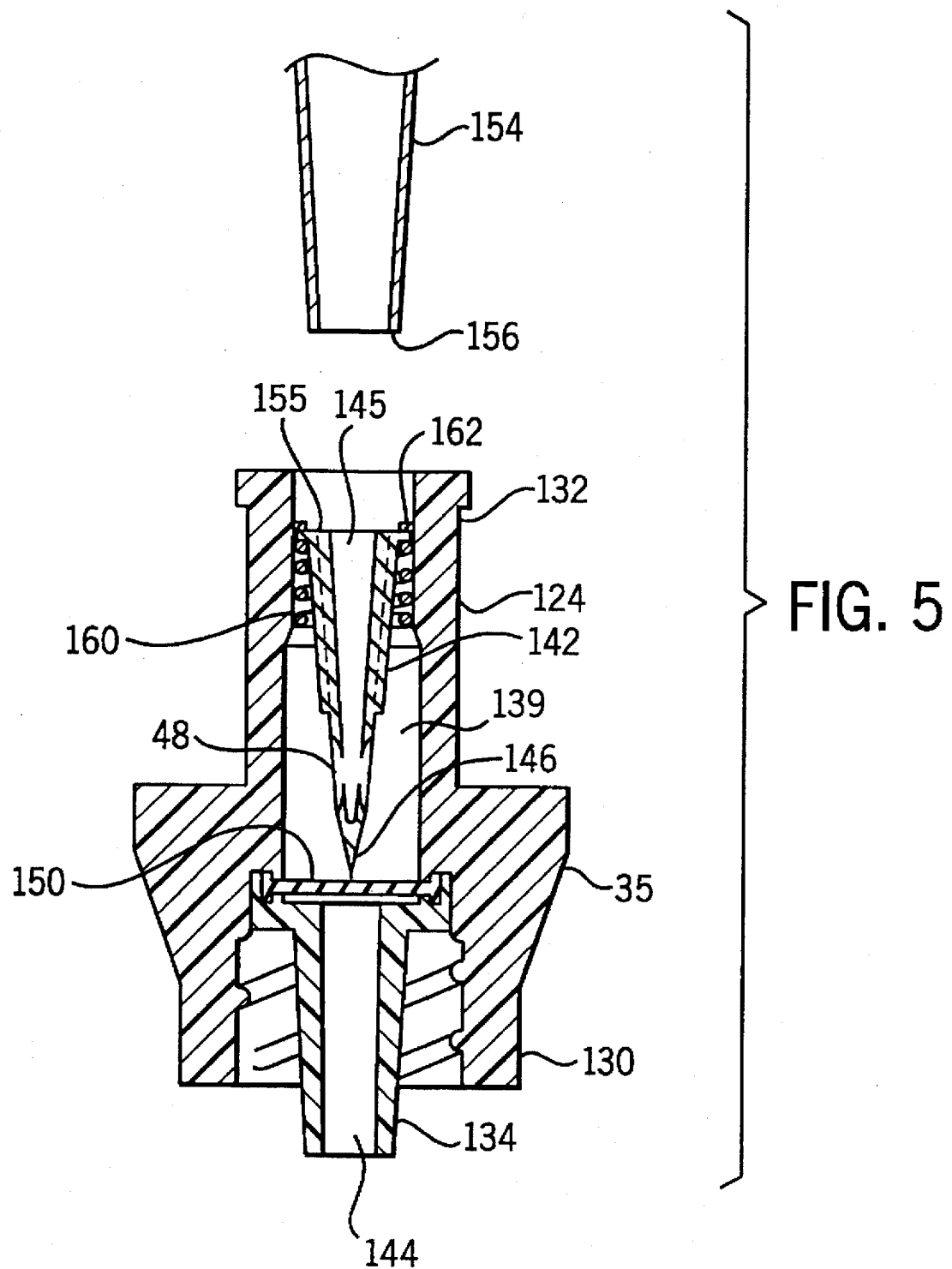
FIG. 5 is a cross-sectional view of an alternative embodiment of a second connector constructed in accordance with the present invention.

Although second connector 24 of the preferred embodiment of the present invention is a CLAVE™ needleless connector, it will be appreciated that other forms of second connector 24 can be used without departing from the intended scope of the present invention as claimed herein. For example, the embodiment of second connector 24 depicted in FIGS. 3 and 4 can be modified, as depicted in FIG. 5. In this embodiment, second connector 124 defines chamber 139 therein. Pierceable closure 150 is disposed across chamber 139 and fluidly seals chamber 139. Pierceable closure 150 is constructed of a resilient, preferably elastomeric, biocompatible material. Protruding member 34 and piercing member 42 of the embodiment depicted in FIGS. 3 and 4 are replaced with movable piercing member 142 which is slidably mounted within chamber 139. Movable piercing member 142 has a piercing tip 146 which is positioned proximally to pierceable closure 150. Fluid flow channel 145 is defined through movable piercing member 142.

First end portion 130 of second connector 124 is configured for attachment to second end portion 18 of conduit 14. As with the preferred embodiment of the present invention depicted in FIGS. 3 and 4, second end portion 18 of conduit 14 can be fluidly connected to first end portion 130 of connector 124 in a variety of ways. For example, protruding member 134 can be disposed at first end portion 130 of connector 124 as depicted in FIG. 5. Protruding member 134 is configured such that second end portion 18 of conduit 14 can be frictionally attached thereto by sliding second end portion 18 of conduit 14 over the outer surface of protruding member 134. As above-discussed with respect to the preferred embodiment of the present invention, second end portion 18 of conduit 14 can also be threadingly or adhesively attached to protruding member 134. Protruding member 134 defines a fluid flow channel 144 therethrough. Fluid flow channel 144 is in fluid contact with pierceable closure 150.

Second end portion 132 of second connector 124 is configured for attachment to a male luer member or syringe 154. In the alternative embodiment depicted in FIG. 5, piercing member 142 has a substantially annular distal edge 155 positioned within chamber 139 within second end portion 132 of second connector 124. Annular distal edge 155 is configured to engage in substantial end-to-end abutment a distal edge 156 of male luer member or syringe 154, as depicted in FIG. 5. Annular distal edge 155 can include a resilient material in order to provide a substantially fluid-tight seal with male luer member or syringe 154 when in engagement therewith. In order to secure male luer member or syringe 154 to second connector 124, mating threads can be formed on second connector 124 and male luer member or syringe 154.

As male luer member or syringe 154 is urged into second connector 124, distal edge 156 engages distal edge 155 and urges piercing member 142 toward pierceable closure 150. Continued movement of male luer member or syringe 154 into second connector 124 will cause piercing tip 146 to pierce pierceable closure 150. When piercing tip 146 pierces pierceable closure 150, fluid flow channel 145 and fluid flow channel 144 are placed in fluid communication through aperture 148 defined through piercing member 142.

In order to ensure that second connector 124 does not permit flow of fluid therethrough when male luer member or syringe 154 is not connected thereto, piercing member 142 is preferably configured such that it is withdrawn from piercing closure 150 when male luer member or syringe 154 is disconnected from second connector 124. For example, a compression spring 160 can be provided within second connector 124 to urge piercing member 142 to a first, non-piercing position when male luer member or syringe 154 is not connected to second connector 124. In order to prevent piercing member 142 from being removed from second connector 124 upon disconnection of male luer member or syringe 154 therefrom, a stop can be provided. It will be appreciated that disconnection of the syringe or luer member from second connector 124 will be facilitated by the configuration of the present invention due to the substantial end-to-end abutment therebetween which minimizes the respective surface areas of the second connector and the syringe or luer member that may become stuck when fluid is directed from the second connector to the syringe or luer member.

The present invention further includes transfer set 12 depicted in FIG. 2. Transfer set 12 includes conduit 60 having a first end portion 62 and a second end portion 64. First end portion 62 is configured for fluid attachment to second connector 24. Male luer member 66 is mounted on first end portion 62 and is configured to attach to either of the embodiments of the present invention depicted herein. In order to secure male luer member 66 to second connector 24, a threaded member 68 is provided on male luer member 66. Threaded member 68 is configured to threadingly engage threads formed on second connector 24. Second end portion 64 of transfer set 12 is preferably configured for attachment to an apparatus constructed to deliver a pharmaceutical product to a patient. For example, second end portion 64 can be configured for attachment to a catheter which delivers a pharmaceutical product intravenously to a patient. In the alternative, second end portion 64 can be configured for attachment to a manifold syringe used to inject a pharmaceutical product into a patient. It will be appreciated that the configuration of second end portion 64 can be varied dependent upon the apparatus to which second end portion 64 is to be attached.

In the embodiment of transfer set 12 depicted in FIG. 2, fluid flow control device 70 is provided along conduit 60. Fluid flow control device 70 preferably provides control of the rate of fluid flow through conduit 60. Fluid flow control device 70 can be a variety of known devices. For example, fluid flow control device 70 can be a CAIR® clamp distributed by Abbott Laboratories. One of ordinary skill in the art will appreciate that other types of fluid flow control devices can be substituted without departing from the spirit and scope of the present invention.

One-way valve 72 is provided in conduit 60 in order to prevent flow from second end portion 64 to first end portion 62. One-way valve 72 can be any of a variety of known valve devices. One-way valve 72 prevents the migration of contaminating elements from second end portion 64 to first end portion 62 of conduit 60, and thereby prevents such contaminating elements from entering access tube set 10. As a result, access tube set 10 can be reused in a plurality of procedures using different transfer tube sets 12.

The present invention also includes a method for delivering a pharmaceutical product from a primary container to a patient. For example, the pharmaceutical product may be an imaging agent such as iopamidol. The method of the present invention includes the step of providing an access tube set constructed in accordance with one of the above-discussed embodiments of the apparatus of the present invention. Also provided is a primary fluid container containing the pharmaceutical product to be delivered to the patient. The access tube set is fluidly connected to the primary container so as to establish fluid communication between the primary container and the conduit defined by the access tube set.

In order to deliver the pharmaceutical product to the patient, the method of the present invention further includes the step of introducing a male luer member into the second connector of the access tube set. As above-discussed, the male luer member may be a part of a tube set such as the transfer tube set of the present invention, or the male luer member may be a part of a syringe. Where the male luer member is a syringe, the syringe is provided and is urged into the second connector such that the syringe engages the second connector in substantial end-to-end abutment. The syringe is then used to draw the pharmaceutical product from the access tube set, through the second connector, and into the syringe. The syringe is then disconnected from the second connector and the pharmaceutical product is delivered to the patient directly or indirectly according to known methods.

Where the male luer member is a transfer tube set, a male luer member on the transfer tube set is urged into the second connector so as to connect fluidly the second connector of the access tube and the transfer tube set such that the luer member of the transfer set is in substantial end-to-end abutment with the second connector. After a medically sufficient volume of pharmaceutical product has been delivered through the transfer tube set to the patient, the transfer tube set is disconnected from the access tube set. The access tube set may be then used in further procedures with separate fluid transfer sets, with separate luer members, or with separate syringes.

Although the present invention has been described herein with respect to certain preferred embodiments, it will be apparent to one of ordinary skill in the art that various modifications are possible without departing from the intended spirit and scope of the present invention as claimed in the appended claims.

What is claimed is:

1. A fluid delivery set comprising:
   a conduit defining a fluid flow path, said conduit having a first end portion and a second end portion;
   a first connector mounted on said first end portion of said conduit, said first connector being fluidly connectable to a source of fluid, said first connector defining a fluid flow path therethrough, said fluid flow path defined by said first connector in fluid communication with said fluid flow path defined by said conduit; and
   a second connector having a first end portion and a second end portion, said first end portion of said second connector mounted on said second end portion of said conduit, said second connector defining a fluid flow path therethrough, said fluid flow path defined by said second connector being in fluid communication with said fluid flow path defined by said conduit, a pierceable seal disposed in and fluidly sealing said fluid flow path defined by said second connector, said second connector further including a piercing member having a piercing tip, said piercing member defining a fluid flow path therethrough, said piercing member disposed in said fluid flow path defined by said second connector, said piercing tip being disposed on a first side of said pierceable seal when said pierceable seal is in a first position, said pierceable seal being movable from said first position to a second position by a male luer member inserted into said second end of said second connector, said pierceable seal being pierceable by said piercing tip as said pierceable seal is moved from said first position to said second position, said piercing tip being disposed on a second side of said pierceable seal when said pierceable seal is in said second position, said piercing member establishing fluid communication through said pierceable seal when said pierceable seal is in said second position.

2. A fluid delivery set in accordance with claim 1, wherein said set further comprises:
   a transfer tube set, said transfer tube set comprising:
      a conduit defining a fluid flow path, said conduit having a first end portion and a second end portion;
      a male luer member mounted on said first end portion of said conduit, said male luer member constructed to move said pierceable seal from said first position to said second position, said male luer member defining a fluid flow path therethrough, said fluid flow path defined by said male luer member fluidly connecting said fluid flow path defined by said second connector and said fluid flow path defined by said conduit of said transfer tube set when said pierceable seal is in said second position; and
      a connector mounted on said second end portion of said conduit.

3. A fluid delivery set in accordance with claim 2, wherein said transfer set further comprises a fluid flow control device disposed on said conduit intermediate said male luer member and said connector.

4. A fluid delivery set in accordance with claim 2, wherein said transfer set further comprises a one-way valve mounted in said fluid flow path defined by said conduit at a position intermediate said male luer member and said connector.

5. A fluid delivery set in accordance with claim 1, wherein said second connector further comprises a protruding member extending outwardly from said second chamber, said protruding member defining a fluid flow path therethrough, said fluid flow path defined through said second connector comprising said fluid flow path defined by said protruding member, said protruding member being connectable to said second end portion of said conduit.

6. A fluid delivery set comprising:
  a conduit defining a fluid flow path, said conduit having a first end portion and a second end portion;
  a first connector mounted on said first end portion of said conduit, said first connector being fluidly connectable to a source of fluid, said first connector defining a fluid flow path therethrough, said fluid flow path defined by said first connector being in fluid communication with said fluid flow path defined by said conduit; and
  a second connector having a first end portion and a second end portion, said first end portion of said second connector mounted on said second end portion of said conduit, said second connector defining a fluid flow path therethrough, said fluid flow path defined by said second connector being in fluid communication with said fluid flow path defined by said conduit, a pierceable seal disposed in and fluidly sealing said fluid flow path defined by said second connector, said second connector further including a piercing member having a piercing tip mounted on a proximal end portion of said piercing member, said piercing member movably disposed in said fluid flow path defined by said second connector, said piercing member defining a fluid flow path therethrough, said piercing member being movable between a first position and a second position, said piercing member having a distal end portion constructed to be engageable in substantial end-to-end abutment by a male luer member inserted into said second connector at said second end portion of said second connector, said piercing member being movable between said first and second positions by a male luer member inserted into said second connector at said second end portion of said second connector, said piercing tip being disposed on a first side of said pierceable seal when said piercing tip is in said first position, said pierceable seal being pierceable by said piercing tip as said piercing member is moved by a male luer member from said first position to said second position, said piercing tip being disposed on a second side of said pierceable seal when said piercing member is in said second position, said piercing member establishing fluid communication through said pierceable seal when said pierceable seal is in said second position.

7. A fluid delivery set in accordance with claim 6, wherein said set further comprises:
  a transfer tube set, said transfer tube set comprising:
    a conduit defining a fluid flow path, said conduit having a first end portion and a second end portion;
    a male luer member mounted on said first end portion of said conduit, said male luer member constructed to move said piercing member from said first position to said second position, said male luer member defining a fluid flow path therethrough, said fluid flow path defined by said male luer member fluidly connecting said fluid flow path defined by said second connector and said fluid flow path defined by said conduit of said transfer tube set when said piercing member is in said second position; and
    a connector mounted on said second end portion of said conduit.

8. A fluid delivery set in accordance with claim 7, wherein said transfer set further comprises a fluid flow control device disposed on said conduit intermediate said male luer member and said connector.

9. A fluid delivery set in accordance with claim 7, wherein said transfer set further comprises a one-way valve mounted in said fluid flow path defined by said conduit at a position intermediate said male luer member and said connector.

10. A method for delivering fluid from a primary container to a patient, said method comprising the steps of:
  providing an access tube set, said access tube set comprising:
    a conduit defining a fluid flow path, said conduit having a first end portion and a second end portion;
    a first connector mounted on said first end portion of said conduit, said first connector being fluidly connectable to a source of fluid, said first connector defining a fluid flow path therethrough, said fluid flow path defined by said first connector in fluid communication with said fluid flow path defined by said conduit; and
    a second connector having a first end portion and a second end portion, said first end portion of said second connector mounted on said second end portion of said conduit, said second connector defining a fluid flow path therethrough, said fluid flow path defined by said second connector being in fluid communication with said fluid flow path defined by said conduit, a pierceable seal disposed in and fluidly sealing said fluid flow path defined by said second connector, said second connector further including a piercing member having a piercing tip, said piercing member disposed in said fluid flow path defined by said second connector, said piercing member defining a fluid flow path therethrough, said piercing tip being disposed on a first side of said pierceable seal when said pierceable seal is in a first position, said pierceable seal being movable from said first position to a second position by a male luer member inserted into said second end of said second connector, said pierceable seal being pierceable by said piercing tip as said pierceable seal is moved from said first position to said second position, said piercing tip being disposed on a second side of said pierceable seal when said pierceable seal is in said second position, said piercing member providing fluid communication through said pierceable seal when said pierceable seal is in said second position;
  inserting a male luer member into said second end portion of said second connector;
  drawing a volume of fluid into said male luer member from said access tube set;
  disconnecting said male luer member from said second connector; and
  delivering said volume of fluid from said male luer member to a patient.

11. A method for delivering fluid from a primary container to a patient, said method comprising the steps of:

a conduit defining a fluid flow path, said conduit having a first end portion and a second end portion;

a first connector mounted on said first end portion of said conduit, said first connector being fluidly connectable to a source of fluid, said first connector defining a fluid flow path therethrough, said fluid flow path defined by said first connector being in fluid communication with said fluid flow path defined by said conduit; and a second connector having a first end portion and a second end portion, said first end portion of said second connector mounted on said second end portion of said conduit, said second connector defining a fluid flow path therethrough, said fluid flow path defined by said second connector being in fluid communication with said fluid flow path defined by said conduit, a pierceable seal disposed in and fluidly sealing said fluid flow path defined by said second connector, said second connector further including a piercing member having a piercing tip mounted on a proximal end portion of said piercing member, said piercing member defining a fluid flow path therethrough, said piercing member movably disposed in said fluid flow path defined by said second connector, said piercing member being movable between a first position and a second position, said piercing member having a distal end portion constructed to be engageable in substantial end-to-end abutment by a male luer member inserted into said second connector at said second end portion of said second connector, said piercing member being movable between said first and second positions by a male luer member inserted into said second connector at said second end portion of said second connector, said piercing tip being disposed on a first side of said pierceable seal when said piercing tip is in said first position, said pierceable seal being pierceable by said piercing tip as said piercing member is moved by a male luer member from said first position to said second position, said piercing tip being disposed on a second side of said pierceable seal when said piercing member is in said second position, said piercing member establishing fluid communication through said pierceable seal when said pierceable seal is in said second position;

inserting a male luer member into said second end portion of said second connector;

drawing a volume of fluid into said male luer member from said access tube set;

disconnecting said male luer member from said second connector; and delivering said volume of fluid from said male luer member to a patient.

* * * * *